United States Patent [19]

Daisy, Jr. et al.

[11] Patent Number: 5,785,995
[45] Date of Patent: Jul. 28, 1998

[54] PHARMACEUTICAL TABLET OF AMIODARONE SALT

[75] Inventors: Samuel Daisy, Jr., Minneapolis; William J. Tourek, Plymouth, both of Minn.

[73] Assignee: Upsher-Smith Laboratories, Inc., Minneapolis, Minn.

[21] Appl. No.: 827,749

[22] Filed: Apr. 11, 1997

[51] Int. Cl.$^6$ .................................................. A61K 9/20
[52] U.S. Cl. ...................... 424/464; 424/489; 424/479; 424/474; 424/463
[58] Field of Search ............................ 424/464, 489, 424/479, 490, 474, 463

[56] References Cited

U.S. PATENT DOCUMENTS 5,085,869 2/1992 Olthoff et al. ..................... 424/499
5,198,228 3/1993 Urban et al. .

OTHER PUBLICATIONS

"Cordarone™ (amiodarone HCl) Tablets", Information Sheet from Wyeth Laboratories, Inc., Philadelphia, 2 pgs. (1994).

Wadke et al., "Preformulation Testing", In: *Pharmaceutical Dosage Forms—Tablets*, vol. 1, edited by H.A. Lieberman et al., Marcel Dekker, Inc., New York, pp. 13–16 (1980).

Lachman, L., et al., "Tablets—Wet Granulation", In: *The Theory and Practice of Industrial Pharmacy*, Lea & Febiger, Philadelphia, pp. 320–324 (1986).

*Primary Examiner*—Carlos A. Azpuru
*Assistant Examiner*—Brian K. Seidleck
*Attorney, Agent, or Firm*—Schwegman, Lundberg, Woessner & Kluth, P.A.

[57] ABSTRACT

An orally administered tablet comprising a therapeutic amount of a pharmaceutically acceptable salt of amiodarone (e.g., an acid salt of amiodarone such as amiodarone hydrochloride) is described. Other ingredients include a disaccharide which is preferably a reducing disaccharide, pregelatinized starch, and an alkali metal starch glycolate. The tablet preferably also comprises at least one of the following: a) 2 to 6% by weight stearic acid, b) less than 1% by weight magnesium stearate, c) 2 to 25% by weight of wet binder, and d) less than 0.1% by weight of silica gel.

20 Claims, No Drawings

PHARMACEUTICAL TABLET OF AMIODARONE SALT

BACKGROUND OF THE INVENTION

1. Field of the Invention

The present invention relates to oral dosing of pharmaceuticals and especially to the compacted tablet dosing of pharmaceutically acceptable salts of amiodarone, such as amiodarone hydrochloride.

2. Background of the Invention

Pharmaceutically active ingredients are conveniently and commonly provided to patients in oral dosages. These dosages are commonly provided in powder, solution, tablet, and capsule forms, depending upon the properties of the active ingredient and medically recommended methods of ingestion to achieve optimum pharmacological effects, patient convenience, and patient acceptability. Tabletting is a particularly convenient method of providing medication to patients in an easily ingested and fast acting form, at least for those types of medication which can tolerate some degree of environmental (especially aerial) exposure, with or without protective coatings on the tablets.

Tablets are generally formed by compaction and/or molding of the active ingredient and other materials generally useful for shaping, holding (binding), and releasing the materials when ingested. Tablets may comprise, for example, an active ingredient, a binder (e.g., pregelatinized starch), lubricant (e.g., stearic acid for facilitating molding), colloidal silica and/or silica gel to retain moisture compatibility, dyes, water softenable/soluble binders such as polyvinylpyrrolidone (e.g., as sold under the trademark of "Povidone™" or "Kollidon™"), and the like.

Amiodarone salts fall within a class of antiarhythmatic with predominantly class III oral administration. Pharmaceutically acceptable salts of amiodarone have been found to be able to alleviate (prevent or suppress) exponential cardiac arhythmia in animals by prolongation of the myocardial coil-action potential duration and refractory period, and non-competitive alpha and beta adrenergic inhibition.

The action of drugs, including the amiodarone class, is based on the delivery and presence of the therapeutically active ingredient into the patient. The single active ingredient may be delivered, or there may be combinations of active ingredients to provide the therapeutic effect. Additional materials, as noted before, may be necessary to put the active ingredient into a deliverable form. As has been reported in U.S. Pat. No. 5,085,869, not all pharmaceutical powder materials can be easily processed in powder form. This difficulty may be primarily due to lack of flowability in the powder (thereby resisting the procedure needed for tablet formation), lack of solubility, and other physical features. It is therefor known in the art to convert the powders into granulates with other materials which combine to have the proper flow properties and then form a tablet from the composition.

To provide a solid consistency to tablets, a wet binding substance is conventionally used in the granulation mixture, especially when the active ingredient might be present in relatively high concentrations within the tablet. Further information on these procedures can be found in H. A. Lieberman and L. Lachman, *Pharmaceutical Dosage Forms*, (1980), Vol. 1, pp.113–16 ("Wet Granulation") and L. Lachman, H. A. Lieberman and J. L. Kanig, *The Theory and Practice of Industrial Pharmacy*, 3$^{rd}$ Edition, pp. 320–24 ("Wet Granulation"). Examples of wet binders are natural gums and resins (e.g., gum acacia, gelatin and modified gelatins, starch [both pregelatinized and as a paste], alginate derivatives including sodium alginate, sugars (glucose, lactose, maltose, etc.), tragacanth and soluble cellulosic materials, and synthetic or modified natural polymers such as methyl cellulose, hydroxypropyl cellulose, polyvinylpyrrolidone, polyvinyl alcohol, and the like.

U.S. Pat. No. 5,085,869 describes that, even though wet binders are usually provided in amounts of 1–10% by weight of granulated compositions, it has appeared that tablets made from such compositions show poor disintegration behavior when immersed in water, and indicates that this could be a disadvantage from a biological absorption viewpoint. This problem is addressed by combining a microcrystalline or microfine cellulose into the granulation mixture, in the absence of substantial amounts of wet binding substances. This mixture is also described as providing granulates which have uninterrupted flow through orifices which are 12 mm or less. In Table 1, amiodarone is listed as one of the low aqueous solubility therapeutically active ingredients which can benefit from the use of the cellulosic materials during granulation and tabletting processes.

Amiodarone HCl is also provided commercially in tablet form as Cordarone™ and the tablet is described in the manufacturer's literature as comprising the amiodarone hydrochloride, along with unspecified amounts of colloidal silica dioxide, magnesium stearate, lactose, starch and Povidone™ (polyvinylpyrrolidone).

SUMMARY OF THE INVENTION

The present invention relates to an orally administered tablet comprising a therapeutic amount of a pharmaceutically acceptable salt of amiodarone (e.g., an acid salt of amiodarone such as arniodarone hydrochloride), a disaccharide which is preferably a reducing disaccharide, pregelatinized starch, and an alkali metal starch glycolate. The tablet preferably also comprises at least one of the following: a) 2 to 6% by weight stearic acid, b) less than 1% by weight magnesium stearate, c) 5 to 25% by weight of wet binder, and d) less than 0.1% by weight of silica gel.

DETAILED DESCRIPTION OF THE INVENTION

The tablet of the present invention comprises, for example, 25 to 80% by weight of a pharmaceutically acceptable salt of amiodarone, 4 to 15% by weight of a reducing disaccharide, and 10 to 50% by weight of a mixture of pregelatinized starch and alkali metal starch glycolate in a ratio of from 5:1 to 80:1. Other pharmaceutically inert ingredients within the tablet may include a) 1 to 8% by weight stearic acid (preferably 2.5 to 6%), b) less than 2% and preferably less than 1% by weight magnesium stearate (preferably 0.05 to 0.3%), c) 2 to 25% by weight of wet binder (preferably 3–10%), and d) up to 0.5% but preferably less than 0.1% (including 0%) by weight of silica gel.

The disaccharides useful in the practice of the present invention include all such disaccharides, including both reducing and non-reducing disaccharides. Preferred materials include maltose, lactose and glucose and their conventional derivatives. Such carbohydrate derivatives include, but are not limited to maltosides, isomaltose, maltonic acid, alpha or beta maltose, 2,3,4,6-tetra-O-methyl glucose, 2,3, 5,6-tetra-O-methylgluconic acid, rutinose, melibiose, gentiobiose, methylocta-O-methylmaltose, and the like, as is well understood in the art.

Combinations of pregelatinized starch and the disaccharide can be used in different ratios within the scope of practice of the present invention to influence the in vitro dissolution rates. This is an advantageous control for the tablet manufacturer.

Pregelatinized starch or polyvinylpyrrolidone can be used alone as a binder to enable the manufacture of acceptable granules for use in the tablets. However, the combination of the two materials has been found to provide better particle distribution. This better particle distribution improves the flowability of the particles during manufacture of the tablet. The improved particle size distribution benefits of this combination of materials (along with the other attributes and materials of the invention) was by itself sufficient to improve flowability of the particles. The level of flowability attained was sufficient to remove the need for a glidant, such as the silica materials used in the prior art. Silica may be added, but it is no longer essential to the provision of useful flow properties in the tableting of the arniodarone tablets.

Pregelatinized starch and starch have been previously used as disintegrants in tablets. However, in the use of tablets containing amiodarone, the alkali metal glycolate, especially the sodium starch glycolate, showed better disintegrant properties than the pregelatinized starch or the starch. The alkali metal glycolate also showed a better disintegration rate than any of the other disintegrants used.

Although either magnesium stearate or stearic acid could be used alone as a lubricant in the manufacture of the tablets, the combination of the two lubricants demonstrated better ejection capabilities from the tablet mold and produced more durable tablets, without adversely affecting the dissolution properties of the tablet.

A competitive commercial amiodarone tablet sold under the name of Cordarone™ was compared to a tablet made according to the first example (first table) of the present invention. The stability of dissolution properties for the tablets at elevated temperature and relative humidity (40° C. and 75% relative humidity) were compared. The tablets of the present invention displayed significantly more stable dissolution properties than did the commercial tablets.

COMPARISON OF THE THREE DISCLOSED COMPOSITIONS
FOR THE DELIVERY OF AMIODARONE HYDROCHLORIDE

| INGREDIENT | UPSHER-SMITH (invention) kg(%) | WYETH | GIST BROCADES NV |
|---|---|---|---|
| Amiodarone HCl | 90 (~53.3%) by weight) | 200 mg/tab | (~64%) |
| Silica Gel | 0% | colloidal silica dioxide (indicated) | <.20% |
| Magnesium Stearate | 0.338 (0.2%) | magnesium stearate (indicated) | <1.0% |
| Lactose Monohydrate (sugar) | 16.050 (9.5%) | lactose (indicated) | other sugars (indicated) |
| Corn Starch (pregel.D) | 47.150 (27.94%) | starch (indicated) | starch (paste and pre-gel, indicated) |
| Sodium Starch Glycolate | 1.70(1.0%) | | |
| Stearic Acid | 5.05 (~3%) | 0% | <1.0% |
| Povidone, USP | 8.45 (~5.0%) | Povidone (indicated) | Kollidon CL (indicated) |

The use of the higher amounts of stearic acid than previously used in the tabletting of amiodarone salts facilitates the flow properties of the salt composition without necessarily having to use silica or other special additives. Such flow control materials may, of course, be added by choice, but are not essential to the practice of the present invention. The addition of the alkali metal starch glycolate is a novel component which may assist in the balance of the ingredient composition to assist in the disintegration of the tablet at the same time as possibly aiding in the control of the flow properties necessary for tabletting of the active ingredients.

PRODUCT: EXAMPLE OF A 200 MG TABLET

| MG/ TABLET | CHEMICAL | AMOUNT KG GRAM | |
|---|---|---|---|
| 200.00 | Amiodarone HCl | 149 | 000 |
| 35.625 | Lactose Monohydrate, NF | **26 | 550 |
| 104.775 | Pregelatinized Corn Starch, NF (Starch 1500) | **78 | 100 |
| 0.075 | FD&C Red #40 Dye | 0 | 056 |
| 0.038 | FD&C Yellow #6 Dye | 0 | 028 |
| 3.750 | Sodium Starch Glycolate, NF (Explotab) | **2 | 800 |
| 11.250 | Stearic Acid, NF (Hystrene 5016) | **8 | 400 |
| 0.750 | Magnesium Stearate, NF | 0 | 559 |
| 18.750 | Povidone, USP (Kollidon-30) | **14 | 000 |
| * | Purified Water, USP (solution) | **79 | 850 |
| * | Purified Water, USP (flush) | **41 | 000 |
| * | Purified Water, USP (re-wetting) | **20 | 000 |

375 MG FINAL TABLET WEIGHT
*Removed during the process.
**Weights are rounded to the nearest 0.00 or 0.05 kg because of the scale used.

What is claimed:

1. An orally administered tablet comprising a therapeutic amount of a pharmaceutically acceptable salt of amiodarone, a reducing disaccharide, pregelatinized starch, and an alkali metal starch glycolate, said pregelatinized starch and said alkali metal glycolate being present in total as from 10 to 50% by weight of said tablet and in a weight ratio of from 5:1 to 80:1, respectively.

2. The tablet of claim 1 wherein 1 to 8% by weight stearic acid is present in said tablet.

3. The tablet of claim 1 wherein said salt amiodarone is present as from 25 to 80% by weight of said tablet.

4. The tablet of claim 2 wherein said salt amiodarone is present as from 25 to 80% by weight of said tablet.

5. The tablet of claim 1 wherein at least 0.05% by weight but less than 1% by weight magnesium stearate is present in said tablet.

6. The tablet of claim 2 wherein at least 0.05% by weight but less than 1% by weight magnesium stearate is present in said tablet.

7. The tablet of claim 4 wherein at least 0.05% by weight but less than 1% by weight magnesium stearate is present in said tablet.

8. The tablet of claim 1 wherein 3 to 25% by weight of wet binder is present in said tablet.

9. The tablet of claim 2 wherein 3 to 25% by weight of wet binder is present in said tablet.

10. The tablet of claim 4 wherein 3 to 25% by weight of wet binder is present in said tablet.

11. The tablet of claim 7 wherein 3 to 25% by weight of wet binder is present in said tablet.

12. The tablet of claim 2 wherein up to 0.5% by weight of silica gel is present in said tablet.

13. The tablet of claim 4 which is free of colloidal silica.

14. The tablet of claim 4 wherein up to 0.1% by weight of silica gel is present in said tablet.

15. The tablet of claim 4 wherein said wet binder comprises polyvinylpyrrolidone.

16. The tablet of claim 7 wherein said wet binder comprises polyvinylpyrrolidone.

17. An orally administered tablet comprising 25–75% by weight of a pharmaceutically acceptable salt of amiodarone, 5–15% by weight of a reducing disaccharide, a pregelatinized starch, and an alkali metal starch glycolate, said pregelatinized starch and said alkali metal glycolate being present in total as from 10 to 50% by weight of said tablet and in a weight ratio of from 5:1 to 80:1, respectively.

18. An orally administered tablet comprising 25–75% by weight of a pharmaceutically acceptable salt of amiodarone, 5–15% by weight of a reducing disaccharide, a pregelatinized starch, and an alkali metal starch glycolate, said pregelatinized starch and said alkali metal glycolate being present in total as from 10 to 50% by weight of said tablet and in a weight ratio of from 5:1 to 80:1, respectively, 1 to 8% by weight stearic acid is present in aid tablet, at least 0.05% by weight but less than 1% by weight magnesium stearate is present in said tablet, and 5 and 25% by weight of wet binder is present in said tablet.

19. The tablet of claim 18 wherein said wet binder comprises polyvinylpyrrolidone.

20. The tablet of claim 19 wherein no colloidal silica is present within said tablet.

* * * * *